United States Patent
Nehlen, III

(10) Patent No.: US 9,630,130 B2
(45) Date of Patent: Apr. 25, 2017

(54) MULTI-SEGMENTED TUBE SHEET

(71) Applicant: Paul F. Nehlen, III, Delavan, WI (US)

(72) Inventor: Paul F. Nehlen, III, Delavan, WI (US)

(73) Assignee: Neptune-Benson, LLC, Coventry, RI (US)

( * ) Notice: Subject to any disclaimer, the term of this patent is extended or adjusted under 35 U.S.C. 154(b) by 0 days.

(21) Appl. No.: 15/050,934

(22) Filed: Feb. 23, 2016

(65) Prior Publication Data

US 2016/0166958 A1 Jun. 16, 2016

Related U.S. Application Data

(60) Division of application No. 14/830,956, filed on Aug. 20, 2015, now Pat. No. 9,302,205, which is a
(Continued)

(51) Int. Cl.
*B01D 35/30* (2006.01)
*B01D 35/06* (2006.01)
(Continued)

(52) U.S. Cl.
CPC ........... *B01D 35/30* (2013.01); *B01D 15/361* (2013.01); *B01D 29/018* (2013.01); *B01D 35/06* (2013.01);
(Continued)

(58) Field of Classification Search
CPC .... B01D 15/361; B01D 29/018; B01D 35/06; B01D 35/30; B01D 2201/0446;
(Continued)

(56) References Cited

U.S. PATENT DOCUMENTS 1,947,109 A 2/1934 Potter
2,164,629 A 7/1939 Sibley
(Continued)

FOREIGN PATENT DOCUMENTS

DE 1027699 4/1958
EP 0117821 11/1987
(Continued)

OTHER PUBLICATIONS

Machine translation of EP 1985956 to Neidermayer (obtained 7-16).*
(Continued)

*Primary Examiner* — Lucas Stelling

(57) ABSTRACT

A method of manufacturing a tube sheet by forming a plurality of separate thin tube sheet segments; forming multiple holes in each sheet in a predetermined pattern, each hole for accommodating a tube sheet filter tube; aligning all of the plurality of tube sheet segments so that the hole pattern of each sheet aligns with the hole pattern in all other sheets of the plurality of tube sheet segments; and securing all of the tube sheet segments together to form a unitary tube sheet. A tube sheet construction that includes a plurality of separate thin tube sheet segments, multiple holes being provided in each sheet in a predetermined pattern, each hole for accommodating a tube sheet filter tube, all of the tube sheet segments being aligning so that the hole pattern of each sheet aligns, and fasteners for securing all of the tube sheet segments together. A media layer is provided between adjacent sheet segments.

12 Claims, 15 Drawing Sheets

Related U.S. Application Data continuation-in-part of application No. 14/535,596, filed on Nov. 7, 2014, now Pat. No. 9,149,742.

(60) Provisional application No. 62/063,681, filed on Oct. 14, 2014.

(51) Int. Cl.

| | |
|---|---|
| *B01D 29/01* | (2006.01) |
| *C02F 1/32* | (2006.01) |
| *F28F 9/02* | (2006.01) |
| *F28F 19/01* | (2006.01) |
| *F28F 27/00* | (2006.01) |
| *C02F 1/68* | (2006.01) |
| *F16L 9/00* | (2006.01) |
| *B01D 15/36* | (2006.01) |
| *F28F 9/06* | (2006.01) |
| *F28F 9/16* | (2006.01) |
| *F28D 21/00* | (2006.01) |

(52) U.S. Cl.
CPC ............ *C02F 1/325* (2013.01); *C02F 1/685* (2013.01); *F16L 9/00* (2013.01); *F28F 9/0221* (2013.01); *F28F 9/0229* (2013.01); *F28F 19/01* (2013.01); *F28F 27/00* (2013.01); *B01D 2201/0446* (2013.01); *F28D 2021/005* (2013.01); *F28F 9/06* (2013.01); *F28F 9/16* (2013.01)

(58) Field of Classification Search
CPC  C01F 1/325; C01F 1/685; C01F 1/725; F16L 9/00; F28D 2021/005; F28F 9/0221; F28F 9/0229; F28F 9/06; F28F 9/16; F28F 19/01; F28F 2/007
See application file for complete search history.

(56) References Cited

U.S. PATENT DOCUMENTS

| | | | |
|---|---|---|---|
| 2,228,549 | A | 1/1941 | Young |
| 2,748,950 | A | 6/1956 | Tursky |
| 3,114,415 | A | 12/1963 | Wintzer |
| 3,182,720 | A | 5/1965 | Brown |
| 3,195,624 | A | 7/1965 | Richards et al. |
| 3,326,279 | A | 6/1967 | Eisberg et al. |
| 3,715,033 | A | 2/1973 | Soriente |
| 3,805,889 | A | 4/1974 | Coolidge |
| 3,972,371 | A | 8/1976 | Plegat |
| 4,105,066 | A | 8/1978 | Buhler |
| 4,182,408 | A | 1/1980 | Laber |
| 4,421,160 | A | 12/1983 | Stafford et al. |
| 4,485,547 | A | 12/1984 | Busse |
| 4,609,462 | A | 9/1986 | Flynn |
| 4,635,712 | A | 1/1987 | Baker et al. |
| 4,718,483 | A | 1/1988 | Artusi |
| 4,782,571 | A | 11/1988 | Krips et al. |
| 4,827,605 | A | 5/1989 | Krips et al. |
| 4,871,014 | A | 10/1989 | Sulzberger |
| 5,055,190 | A | 10/1991 | Hayes et al. |
| 5,128,038 | A | 7/1992 | Slavitschek et al. |
| 5,154,679 | A | 10/1992 | Fuller et al. |
| 5,630,470 | A | 5/1997 | Lockwood, Jr. |
| 6,026,804 | A | 2/2000 | Schardt et al. |
| 6,206,086 | B1 | 3/2001 | McKey |
| 7,048,042 | B2 | 5/2006 | Juschka |
| 7,377,039 | B2 | 5/2008 | Al-Anizi et al. |
| 7,712,517 | B2 | 5/2010 | Gandolfi et al. |
| 8,177,932 | B2 | 5/2012 | Becnel et al. |
| 9,127,896 | B1 | 9/2015 | Nehlen, III |
| 9,149,742 | B1 | 10/2015 | Nehlen, III |
| 2004/0238161 | A1 | 12/2004 | Al-Anizi et al. |
| 2005/0034847 | A1 | 2/2005 | Graham et al. |
| 2007/0144716 | A1 | 6/2007 | Doh et al. |
| 2009/0019689 | A1 | 1/2009 | Zobel |
| 2009/0084725 | A1 | 4/2009 | Poklop |
| 2010/0003169 | A1* | 1/2010 | Foster ............... C02F 1/325 422/140 |
| 2010/0243208 | A1 | 9/2010 | Kar et al. |

FOREIGN PATENT DOCUMENTS

| | | |
|---|---|---|
| EP | 0 777 098 | 4/1997 |
| EP | 1265048 | 12/2002 |
| EP | 1 985 956 | 10/2008 |
| FR | 2132528 | 11/1972 |
| FR | 2158722 | 6/1973 |
| FR | 2302186 | 9/1976 |
| JP | 2011-121031 | 6/2011 |
| WO | 93/04333 | 3/1993 |

OTHER PUBLICATIONS

Search Report in EP 15275210.0.
Examiner requisition dated Jun. 6, 2016 in CA2908226.
AU Patent Examination Report No. 1 dated Oct. 26, 2015.
CA Examiner requisition dated Feb. 15, 2016.
CA Examiner requisition dated Jan. 7, 2016.

* cited by examiner

MULTI-SEGMENTED TUBE SHEET

This application is a divisional of U.S. Serial No. 14/830,956, filed Aug. 20, 2015, now U.S. Pat. No. 9,302,205, which is a continuation-in-part (CIP) of U.S. Ser. No. 14/535,596 filed on Nov. 7, 2014, now U.S. Pat. No. 9,149,742, which claims priority to under 35 U.S.C. §119 (e) to commonly owned and U.S. Provisional Patent Application No. 62/063,681 which was filed on Oct. 14, 2014, and which is incorporated by reference herein in its entirety. Reference is also made to application Ser. No. 14/535,655 filed on Nov. 7, 2014, now U.S. Patent No. 9,127,896, and a continuation-in-part (CIP) application thereto of Ser. No. 14/830,994, filed Aug. 20, 2015, now U.S. Pat. No. 9,303,924. All of the above identified applications are incorporated by reference herein in their entirety.

FIELD OF THE INVENTION

The present invention relates in general to tube sheets that are typically used in such applications as filtration and heat exchange. More particularly, the present invention relates to an improvement in the construction of a tube sheet that enhances the function of the tube sheet and enables the tube sheet to be manufactured with less expense. Even more particularly the present invention relates to an improved tube sheet construction for providing greater process control by employing an active media layer for a tube sheet used in particular in a filtration construction.

BACKGROUND OF THE INVENTION

In the field of filtration and heat exchange, there is a device commonly used to develop separate regions; commonly referred to as a tube sheet. The tube sheet is meant to be supported in a housing or tank and is used primarily for the support of a plurality of filter elements that are usually in the form of filter tubes for filtration or heat exchange. By way of example refer to U.S. Pat. Nos. 3,715,033; 4,609,462 and 5,128,038 which describe various filter constructions in which the filter tubes are supported by the tube sheet essentially forming a boundary region by which filtration or even heat exchange can be affected. The tube sheet provides a support for the tubes, but also functions as a bulkhead to the media on either side of the tube sheet; effectively maintaining a discontinuity so that transformation can take place.

In actual operation, there are times when differential pressures on opposing sides of the tube sheet are in excess of normal operating differential pressures; substantial pressures in and of themselves. In order to overcome the differential pressure and maintain structural rigidity the tube sheet is typically produced of a substantial thickness, and machined to a high tolerance to accept the tubes. One particular disclosure of a tube sheet is shown in the '462 patent as tube sheet 32.

This tube sheet thickness solves the problem of structural rigidity while simultaneously serving the purpose of a bulkhead and a means to maintain the spacing between the tubes. This comes at a cost. The machining process which typically is by drilling or water jet cutting is a slow and costly process to produce the sufficiently rigid, high tolerance barrier required.

In a typical tube sheet construction the tube sheet may be formed of a metal material such as stainless steel and can have a thickness on the order of ½ inch. A sheet of stainless steel is fabricated to various diameters; between less than one foot in diameter up to a diameter of greater than 5 feet in diameter, and then holes [one to 2500 or more holes] are drilled with a conventional drill bit or water jet cutter to facilitate insertion of the tube elements. This process is cumbersome and very time consuming; as much as 20 hours or more to produce one sheet 5 feet in diameter.

The vast majority of tube sheets in use are fabricated in this fashion, whether it is for use in a heat exchanger, filter, for reverse osmosis, distillation, or as a condenser, evaporator, or for fuel cell applications. An objective of the present invention is to provide a multi-segment tube sheet wherein, instead of drilling a one-piece thick plate, the tube sheet is formed in multiple segments which are then fastened together to provide structural rigidity.

Another objective of the present invention is to provide an improved tube sheet which eliminates the costly and time consuming steps to manufacture as with present day tube sheets.

Still another objective of the present invention is to provide an improved tube sheet structure including a stacked assembly of thinner sheets, that when assembled together provide the structural integrity of the present day tube sheet but at a substantially manufacturing reduced cost.

A further objective of the present invention is to provide an improved tube sheet structure including a stacked assembly of thinner sheets, and in which the thinner sheets are more readily processed for creating holes therein such as by being punched on an automated press, burned with a laser or a plasma cutter, or formed by being printed using additive manufacturing technologies; ie 3D printing as but one example.

Another objective of the present invention is to provide an improved tube sheet construction including an interstitial layer referred to herein as a media layer so that the tube sheet functions both as a tube sheet as well as a multifunctional processing device.

A further objective of the present invention is to provide an improved tube sheet construction that provides, in addition to multiple sheet segments, a unique intermediate layer referred to herein as a media layer for providing any one of a number of additional functions including, but not limited to, filtration, flow control, shock absorption, magnetic characteristics, dosing, chemical or medical treatment, or ion exchange.

SUMMARY OF THE INVENTION

To accomplish the foregoing and other objects, features and advantages of the present invention there is provided an improved tube sheet structure and associated method of manufacturing such a tube sheet, while solving the above mentioned problems associated with present tube sheet constructions. The present invention solves the problem of maintaining the high tolerance, tube spacing, and structural rigidity of the tube sheet. This is achieved in accordance with the present invention by manufacturing the tube sheet out of multiple thinner layers of sheet that are critically aligned to each other and to the tubes in the assembly process, and then fixing this assembly together to achieve the final structural integrity and bulkhead characteristics of a tube sheet.

For the present invention the same end-use tube sheet in this arrangement will take a fraction of the time to manufacture, due primarily to the substantially reduced thickness of individual sheets, if punched on an automated press, burned with a laser or a plasma cutter, or printed using additive manufacturing technologies [ie 3D printing as but one example] and assembled and fixed. An added feature in accordance with the present invention is that layering of the tube sheet allows interstitial placement of materials creating a non-homogeneous device that in its entirety functions both as a tube sheet as well as a multifunctional filtration device or membrane. Fixing the thin sheets into contact serves the purpose of maintaining the bulkhead effect and the structural integrity, as well as the desired tube spacing. One or more fasteners are used to secure all layers or sheets together as a unitary mass functioning as a tube sheet. By "fasteners" reference can be made to any one of a number of devices or techniques by which the individual layers or sheets are secured together.

In accordance with one aspect of the present invention there is provided a method of manufacturing a tube sheet by forming a plurality of separate thin tube sheet segments; forming multiple holes in each sheet in a predetermined pattern, each hole for accommodating a tube sheet filter tube; aligning all of the plurality of tube sheet segments so that the hole pattern of each sheet aligns with the hole pattern in all other sheets of the plurality of tube sheet segments; and securing all of the tube sheet segments together to form a unitary tube sheet.

In still other aspects of the present invention the forming of holes is by means of punching the holes concurrently; by punching the holes on an automated press; by burning with a laser; by means of a plasma cutter; by printing or etching using additive manufacturing technologies such as 3D printing; including inserting a media layer between adjacent sheet segments; including inserting multiple media layers between adjacent sheet segments; wherein the media layer is comprised of a filter layer; and wherein the securing of the layers is by means of at least one of permanently constructed as with rivets, weld, solder, braze, epoxy, or constructed with removable fasteners such as bolts, screws, removable rivets, etc. or simply floated between some reference points to facilitate loading of the media.

In another embodiment of the present invention there is provided a tube sheet construction that includes a plurality of separate thin tube sheet segments, multiple holes being provided in each sheet in a predetermined pattern, each hole for accommodating a tube sheet filter tube, all of the tube sheet segments being aligning so that the hole pattern of each sheet aligns with the hole pattern in all other sheets of the plurality of tube sheet segments, and fasteners for securing all of the tube sheet segments together.

In a further aspect of the present invention including at least one media sheet interposed between adjacent sheet segments; including more than one media sheet disposed respectively between adjacent sheet segments; wherein the media layer comprises a filtration layer clamped between adjacent sheet segments; wherein each sheet segment is planar in shape having a thickness that is an order of magnitude less than a diameter of the tube sheet segment; including means for forming each hole including one of a punch device, a laser cutter, a plasma cutter, and etching device; wherein the securing of the layers is by means of at least one of permanently constructed as with rivets, weld, solder, braze, epoxy, or constructed with removable fasteners such as bolts, screws, removable rivets, etc. or simply floated between some reference points to facilitate loading of the media; including a flange at one end of each filter tube for retaining each filter tube within the tube sheet; wherein the flange is disposed between adjacent sheet segments; and including a cover disposed over all of the sheet segments; and wherein the media layer is formed of one of a layer for filtration, flow control, shock absorption, magnetic characteristics, dosing, chemical or medical treatment, or ion exchange.

In another version of the present invention there is provided a tube sheet construction that is comprised of a plurality of separate planar tube sheet segments, multiple holes being provided in each planar tube sheet segment in a predetermined pattern, each hole for accommodating an elongated tubular element, an active planar layer disposed parallel with the plurality of separate tube sheet segments, and fasteners for securing all of the planar tube sheet segments and the active planar layer together and arranged so that all planar tube sheet segments and said active planar layer are maintained in intimate contact so as to form a solid tube sheet structure. The active layer comprises a UV light emanating layer that doses any fluid flow through the tube sheet construction with UV light emanating from the UV light emanating layer so as to disrupt or annihilate any living matter.

In still another version of the present invention there is provided a tube sheet construction that includes a tube sheet and a plurality of elongated tubular elements supported by the tube sheet, said tube sheet comprised of a plurality of separate planar tube sheet segments, multiple holes being provided in each planar tube sheet segment in a predetermined pattern, each hole for accommodating one of the plurality of elongated tubular elements, all of the tube sheet segments being aligning so that the hole pattern of each segment aligns with the hole pattern in all other segments. In this version the elongated tubular element has a flanged top end and a contiguous tubular shaft with the flanged top end having a diameter greater than a diameter of the tubular shaft. A securing piece may be used and constructed and arranged about the tubular shaft of the elongated tubular element and spaced below the flanged top end of the elongated tubular element. The securing piece is for engagement with the tubular shaft to provide a compressive force against the tube sheet segments that are disposed between the flanged top end of the elongated tubular element and the securing piece.

In still a further version of the present invention there is provided a tube sheet construction that is comprised of a plurality of separate planar tube sheet segments, multiple holes being provided in each planar tube sheet segment in a predetermined pattern, each hole for accommodating an elongated tubular element, a passive planar layer disposed parallel with the plurality of separate tube sheet segments, and fasteners for securing all of the planar tube sheet segments and the passive planar layer together and arranged so that all planar tube sheet segments and said passive planar layer are maintained in intimate contact. The passive layer is formed as a layer impregnated with one of a medical and chemical substance that is released over time. Other aspects include wherein the medical or chemical substance is released over time based on temperature; the tube sheet construction functions as a heat exchanger; the tube sheet construction is in the form of a blood warming device; the medical or chemical substance is released over time based on fluid flow.

BRIEF DESCRIPTION OF THE DRAWINGS

It should be understood that the drawings are provided for the purpose of illustration only and are not intended to define the limits of the disclosure. In the drawings depicting the present invention, all dimensions are to scale. The foregoing and other objects and advantages of the embodiments described herein will become apparent with reference to the following detailed description when taken in conjunction with the accompanying drawings in which.

DETAILED DESCRIPTION

Figure 5:
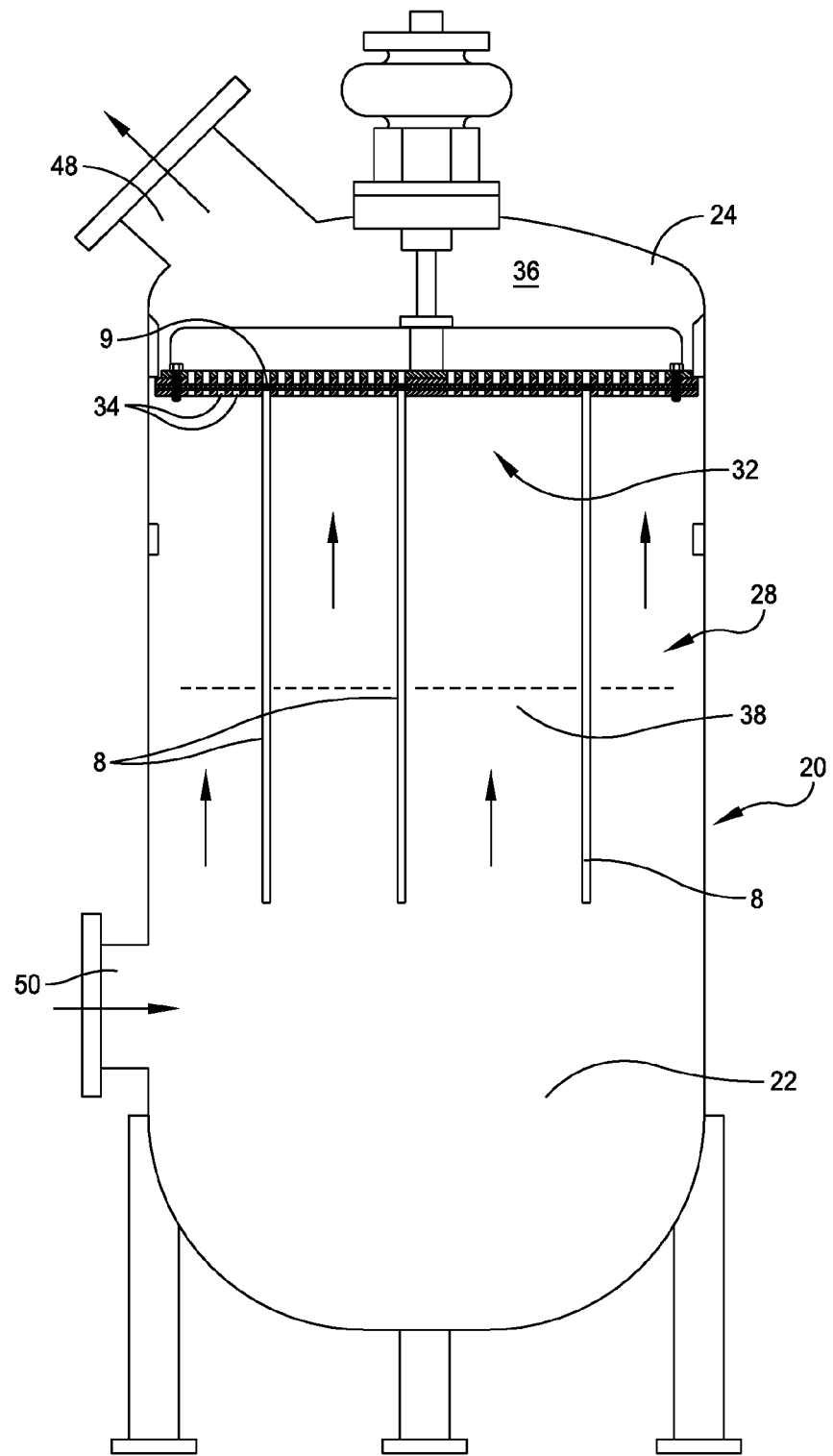
FIG. 5 is a schematic diagram showing the tube sheet as applied to a filter tank.
Figure 6:
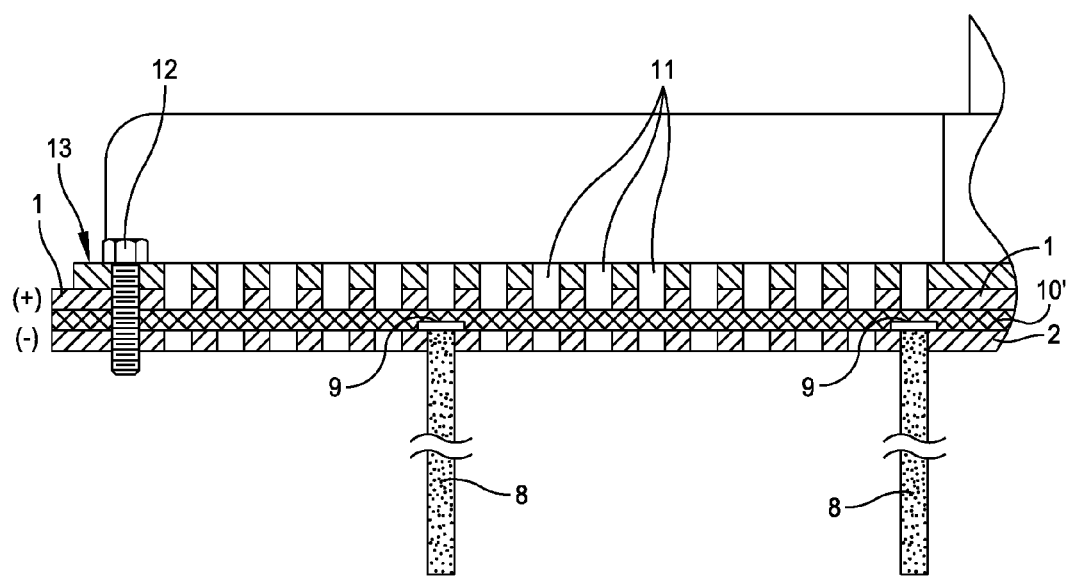
FIG. 6 is a cross-sectional view like that depicted in FIG. 3A where the media layer is a passive layer in the form of a nanotubular structure within a platinum amalgam.

As mentioned before, in accordance with the present invention the tube sheet is constructed out of multiple thinner layers of sheet material that are aligned to each other and to the tubes in the assembly process, and then fixing this assembly together to achieve the final structural integrity and bulkhead characteristics of a tube sheet. In the drawings several different versions of the invention are set forth such as in FIGS. 1-4. FIG. 5 is an illustration of the application of the principles of the present invention to a filtration structure, although it is contemplated that the principles of the present invention can be applied to other systems and devices such as for heat exchange. FIG. 6 shows one alternate embodiment in the form of a nanotubular structure. In connection with the various embodiments of the tube sheet construction shown herein reference is now also made to co-pending application Ser. No. 14/535,655, which is hereby incorporated by reference herein in its entirety, and illustrating the application of the principles of the present invention to a heat exchanger.

Figure 1:
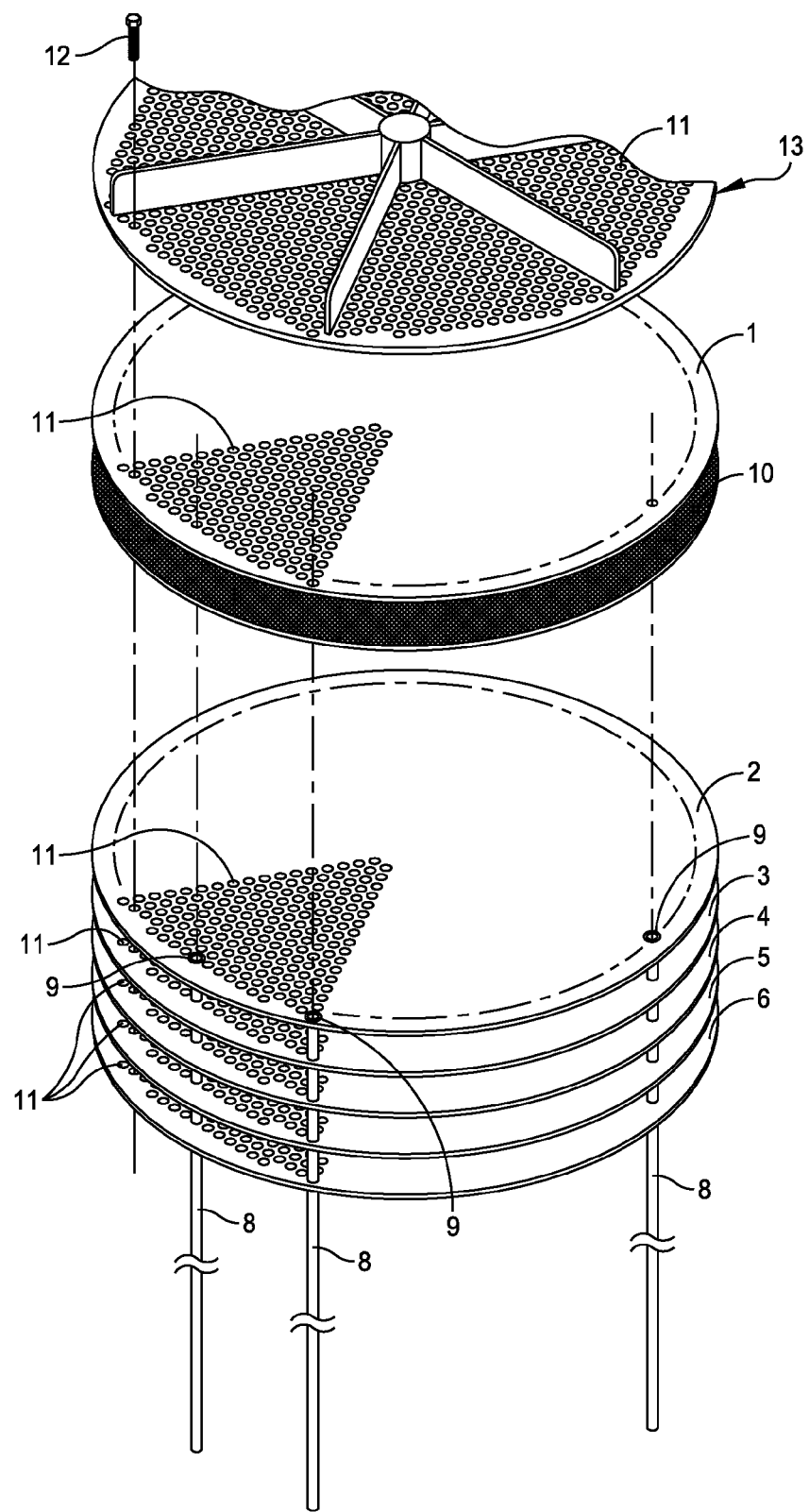
FIG. 1 is a perspective view of a first embodiment of the present invention.

In accordance with one aspect of the present invention there is provided a method of manufacturing a tube sheet by forming a plurality of separate thin tube sheet segments such as shown in FIG. 1 as layers or sheets 1-6. The next step is forming multiple holes in each sheet in a predetermined pattern such as illustrated at 11 in the drawings herein. Each hole 11 is for accommodating a tube sheet tube 8. A next step is aligning all of the plurality of tube sheet segments 1-6 so that the hole pattern of each sheet aligns with the hole pattern in all other sheets of the plurality of tube sheet segments and securing all of the tube sheet segments together to form a unitary tube sheet such as with the use of fasteners 12 in the embodiment of FIG. 1. Most likely several fasteners would be employed throughout the tube sheet in order to provide a secured unitary structure. All fasteners or other securing means is meant to hold all sheets or layers together.

Additionally, one variation of the present invention allows for stacking, not just the tube sheet layers, but in effect the stacking and retention of other filtration or conversion media between the segmented tube sheet layers. This extra media sheet is illustrated in the drawings herein. For instance, progressively finer filter media between the sheets will facilitate backwashing to regenerate the sheets. Alternatively, reactive substances may be layered in the stacks such that contact with this substance alters the media passing through that section. Another possibility that this invention facilitates over the prior art relates to conductive versus insulative materials and the embedding of electronic, magnetic, plasma, unlimited combinations of metals and non-metals, the difference which manifest themselves as a subcomponent of the greater assembly which is that of a segmented tube sheet.

It is noted that the "media" layer, identified herein by a layer 10 in the drawings and also referred to as an interstitial layer, can take on a multitude of forms. This layer is referred to herein in this particular application as being either a "passive layer" or an "active" layer. In either case this layer describes an intermediate layer that is essentially a subcomponent of the whole assembly (tube sheet) but working in concert with the whole assembly to provide unique characteristics not possible with existing tube sheet constructions. A "passive" layer may be considered as one in which, by the selection of different materials for that layer, one can provide different effects upon the fluid flow through the system, while at the same time not being considered as providing any active stimulus or response. An "active" layer, on the other hand, may be considered as one in which either an external stimulus is applied to the layer or a response is elicited from the layer. Examples of a "passive" layer are where the media layer provides filtration, flow control, shock absorption, magnetic characteristics, dosing, chemical or medical treatment, or ion exchange. Examples of an "active" layer are where the media layer is used to sense a parameter within the tube sheet such as pressure or temperature (response) or where the media layer is externally excited such as by applying a magnetic field to the layer (stimulus). Other examples are set forth herein.

For filtration and heat exchange applications it is common to construct the tube sheet of a metal material such as stainless steel. However, in accordance with the present invention the tube sheet, or certain layers thereof, can also be formed of an insulative or non-metal material such as a glass reinforced plastic material. Also, alternating conductive and non-conductive materials for the various layers can be provided, examples of which are set forth later.

For filtration purposes the media layers (reference number 10 in the drawings) can take the form of a single or multiple layup of filter paper or screen material of a woven, matted, or other construction. Alternatively, the media layer can take the form of a bonded nanotubular or amalgam structure with platinum acting as a catalytic agent suppressing H2O conversion to H2 as but one example; while continuing to function as a tube sheet as the superstructure of the device (see FIG. 6). This layer serves as the site of catalysis in a redox reaction providing both expanded surface area and the requisite catalyst, in this case platinum, to enable a reaction that occurs faster and with less energy. Since in the reaction, catalysts regenerate, only a small amount is generally required.

Again, one can envision a circumstance where, in this now discontinuous tube sheet device, the interstitial layer is attached to electrical contacts and the interstitial layer is itself a device that counts passing target molecules. Another envisioned energized interstitial layer senses any number of differences across the breadth of the device; for example, differential pressure where a single heat exchanger utilizes a plurality of tube sheets. Yet another envisioned interstitial layer within one or more layers of the tube sheet could be measuring the temperature differential across the tube sheet and feeding back in real time to enhance computational fluid dynamics software to form an improved open or closed-loop arrangement that enables a new breed of highly interactive tube sheets.

Figure 1A:
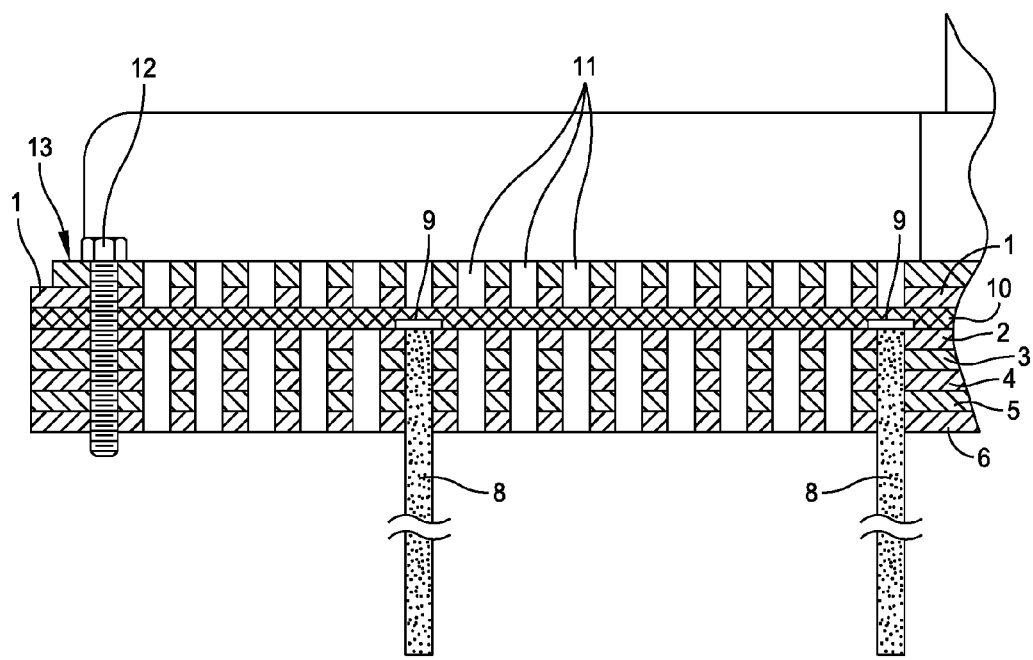
FIG. 1A is a cross-sectional view through the tube sheet of FIG. 1 as taken along line 1A-1A.

FIGS. 1 and 1A shows a particular version of a multi-segmented tube sheet, where n=2 is the minimum number of sheets and there is no upper limit; and the minimum tube count n=1 and there is no upper limit. In this particular embodiment the multi-segmented tube sheet is shown with six sheets identified as sheets 1 through 6 arranged such that the tubes 8 (themselves at times filtration elements, other times not) are installed. Each tube 8 may be of a type as shown in, for example, U.S. Pat. No. 3,715,033 and in which the filtration occurs through the sidewall of the tube and exits at one end of the tube 8. FIG. 5 is included as an example of the application of the principles of the present invention to a filtration apparatus. In the example provided in FIG. 5 herein the bottom of each tube is blocked so that the only exit from the tube is at a top end thereof into the upper effluent compartment 36.

In addition, in FIGS. 1 and 1A there is shown a single media sheet or layer 10 disposed just below the top sheet 1. In this particular construction the layer 10 is shown thicker than the other sheets 1-6 and is formed of a filtration material. In this particular embodiment there is provided a flanged surface 9 that is disposed on the outer face of the second sheet 2. The first sheet 1 in this case acts as a hold down to the tubular elements 8 and all other sheets including the additional layer of media 10 that may act as a filtration barrier or a conversion medium to the process media as it passes from the unprocessed side to the processed side of the apparatus (see FIG. 5 as an example), and which may or may not be installed at this location depending on the desired action on the media as it transitions from the primary to the secondary side of the tube sheet. The tube sheet stack in the assembled form may be permanently constructed as with rivets, weld, solder, braze, epoxy, etc. (see fasteners 12) or constructed with removable fasteners such as bolts, screws, removable rivets, etc. or simply floated between some reference points to facilitate loading of the media while simultaneously serving the purpose of a traditional tube sheet acting simply as a bulkhead and the demarcation location between the primary and secondary sides of the tube sheet.

FIGS. 1 and 1A also show a myriad of holes at 11 that are considered as extending through the entire tube sheet segments. Although the retention of each tube 8 is shown in FIG. 1A is at a location of the sheet 2, it is understood that the filter tube 8 may be secured at other locations within the tube sheet, such as described in other embodiments disclosed herein. Also shown is a cover 13 that preferably seals the top of the assembly. All fasteners 12 are secured through the cover 13, as shown. The media layer or layers 10 are not meant to have holes therethrough as each is to function as a filter media of some type, or as other types as mentioned herein. Thus, for example, in FIG. 1A the layer 10 is continuous. Also, although each flange is illustrated as recessed in one of the segments, in an embodiment as in FIG. 1, the flange can be positioned resting directly on the top of the surface of segment 2, as the material of layer 10 is usually deflectable. The same also applies to the embodiment shown in FIGS. 3 and 3A. In this embodiment, as well as in other embodiments described herein, the fasteners are arranged so that all separate layers are held in intimate contact with an adjacent layer so as to maintain a solid tube sheet structure without any gaps between layers. This intimate contact also applies to contact with any media layer that is used.

Figure 2:
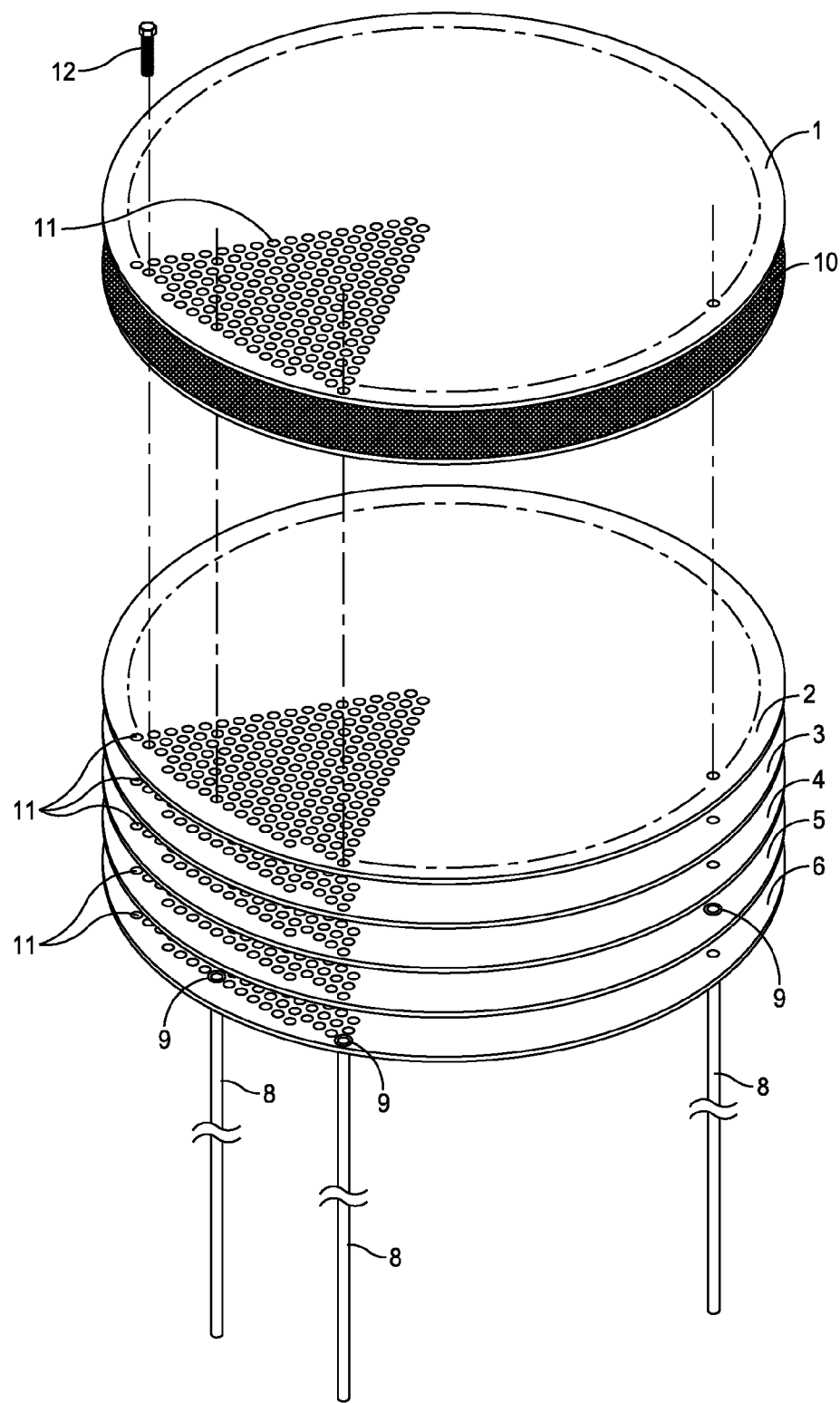
FIG. 2 is a perspective view of a second embodiment of the present invention.
Figure 2A:
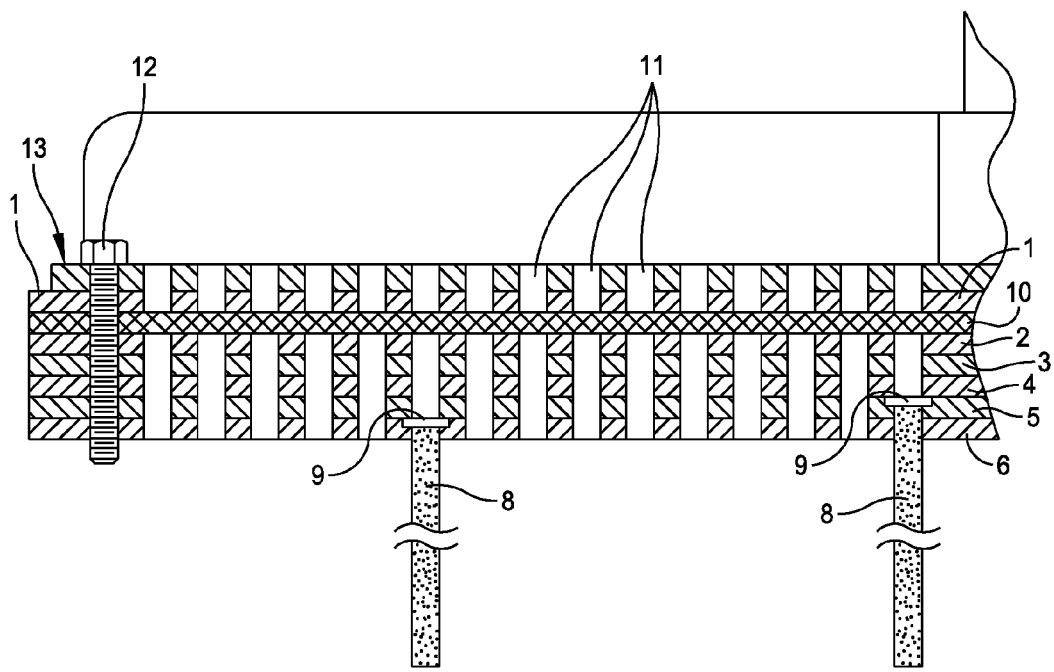
FIG. 2A is a cross-sectional view through the tube sheet of FIG. 2 as taken along line 2A-2A.

FIGS. 2 and 2A shows a second version of a multi-segmented tube sheet, where n=2 is the minimum number of sheets and there is no upper limit; and the minimum tube count n=1 and there is no upper limit. In this particular embodiment the multi-segmented tube sheet is shown with six sheets identified as sheets 1 through 6 arranged such that the tubes 8 (themselves at times filtration elements, other times not) are installed. In addition there is shown a single media sheet or layer 10 disposed just below the top sheet 1. Layer 10 is preferably uniform in construction. In this particular embodiment there is provided a flanged surface 9 that is disposed on the outer face of the fifth sheet 5. The first sheet 1 in this case acts as a hold down to the tubular elements 8 and all other sheets including the additional layer of media 10 that may act as a filtration barrier or a conversion medium to the process media as it passes from the unprocessed side to the processed side, and which may or may not be installed at this location depending on the desired action on the media as it transitions from the primary to the secondary side of the tube sheet. The tube sheet stack in the assembled form may be permanently constructed as with rivets, weld, solder, braze, epoxy, etc. (see fasteners 12) or constructed with removable fasteners such as bolts, screws, removable rivets, etc. or simply floated between some reference points to facilitate loading of the media while simultaneously serving the purpose of a traditional tube sheet acting simply as a bulkhead and the demarcation location between the primary and secondary sides of the tube sheet.

Figure 3:
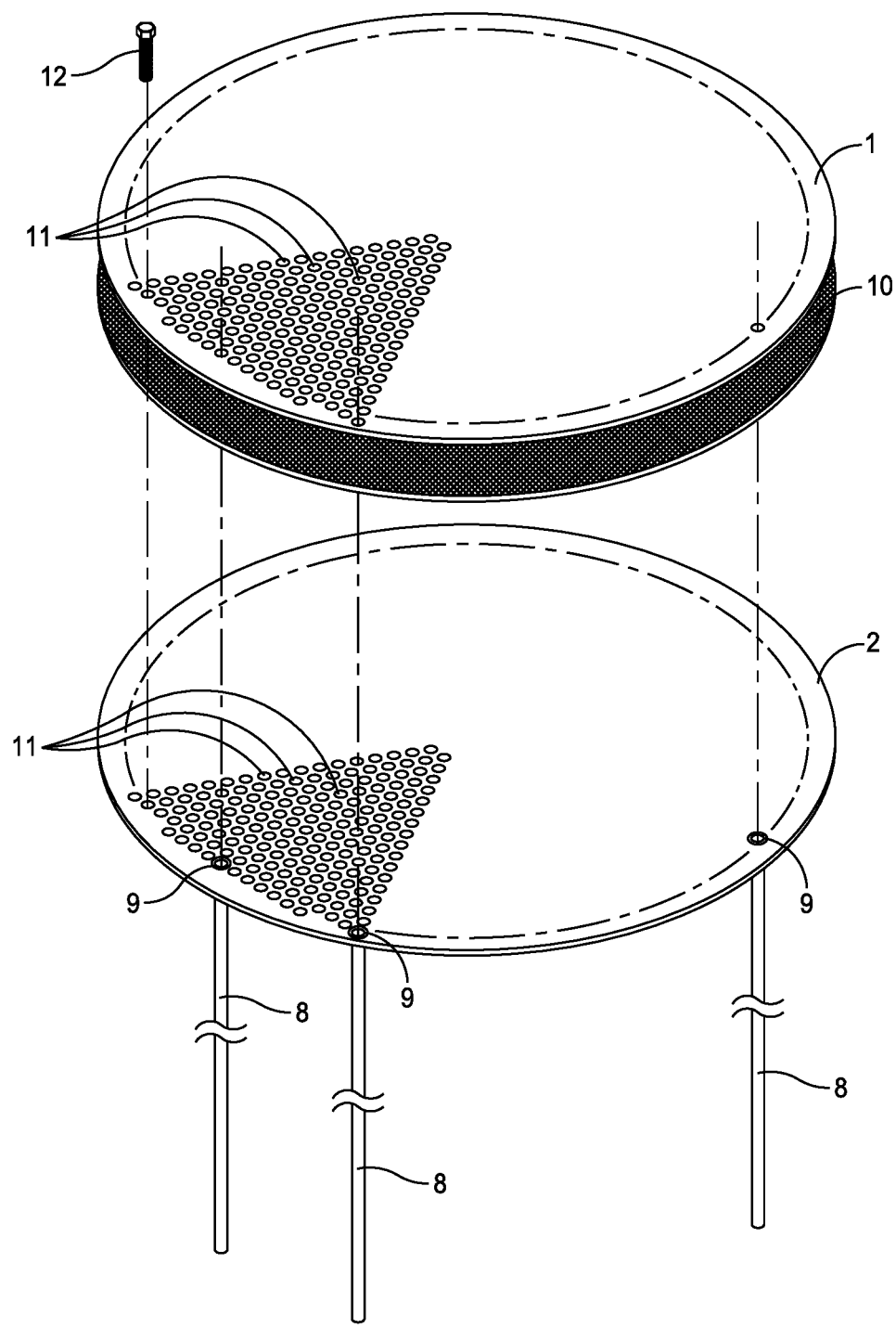
FIG. 3 is a perspective view of a third embodiment of the present invention.
Figure 3A:
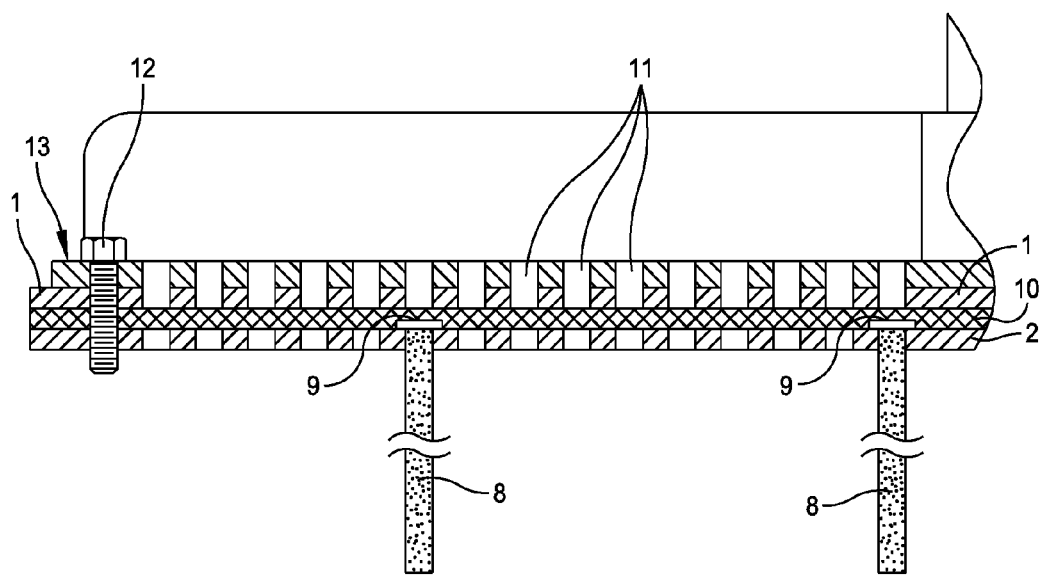
FIG. 3A is a cross-sectional view through the tube sheet of FIG. 3 as taken along line 3A-3A.

FIGS. 3 and 3A shows a third version of a multi-segmented tube sheet, where n=2 is the minimum number of sheets and there is no upper limit; and the minimum tube count n=1 and there is no upper limit. In this particular embodiment the multi-segmented tube sheet is shown with only two main sheets identified as sheets 1 and 2 arranged such that the tubes 8 (themselves at times filtration elements, other times not) are installed. In addition there is shown a single media sheet or layer 10 disposed just below the top sheet 1. In this particular embodiment there is provided a flanged surface 9 that is disposed essentially between the two sheets 1 and 2. The first sheet 1 in this case acts as a hold down to the tubular elements 8 and all other sheets including the additional layer of media 10 that may act as a filtration barrier or a conversion medium to the process media as it passes from the unprocessed side to the processed side, and which may or may not be installed at this location depending on the desired action on the media as it transitions from the primary to the secondary side of the tube sheet. The tube sheet stack in the assembled form may be permanently constructed as with rivets, weld, solder, braze, epoxy, etc. (see fasteners 12) or constructed with removable fasteners such as bolts, screws, removable rivets, etc. or simply floated between some reference points to facilitate loading of the media while simultaneously serving the purpose of a traditional tube sheet acting simply as a bulkhead and the demarcation location between the primary and secondary sides of the tube sheet.

Figure 4:
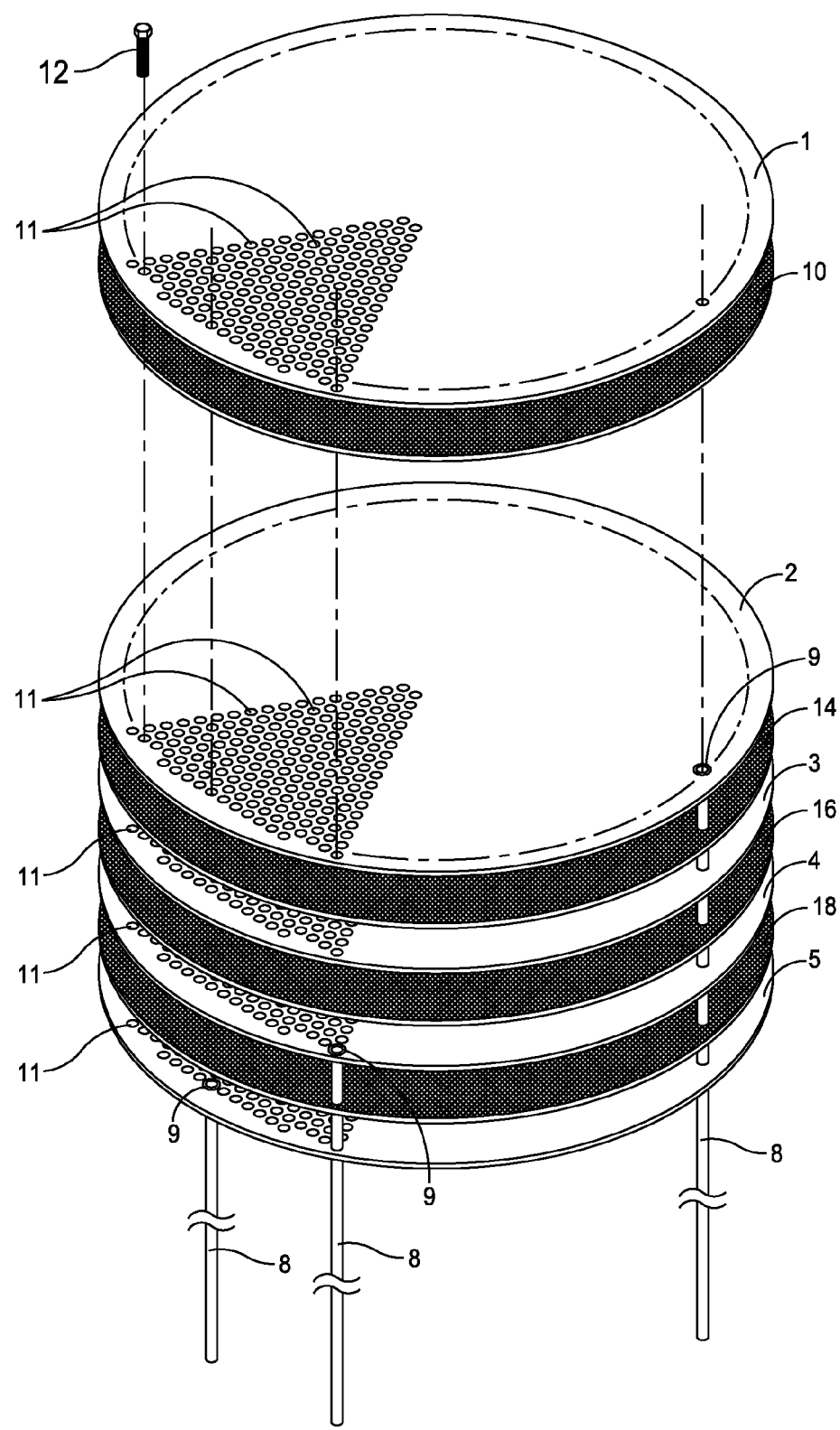
FIG. 4 is a perspective view of a fourth embodiment of the present invention.
Figure 4A:
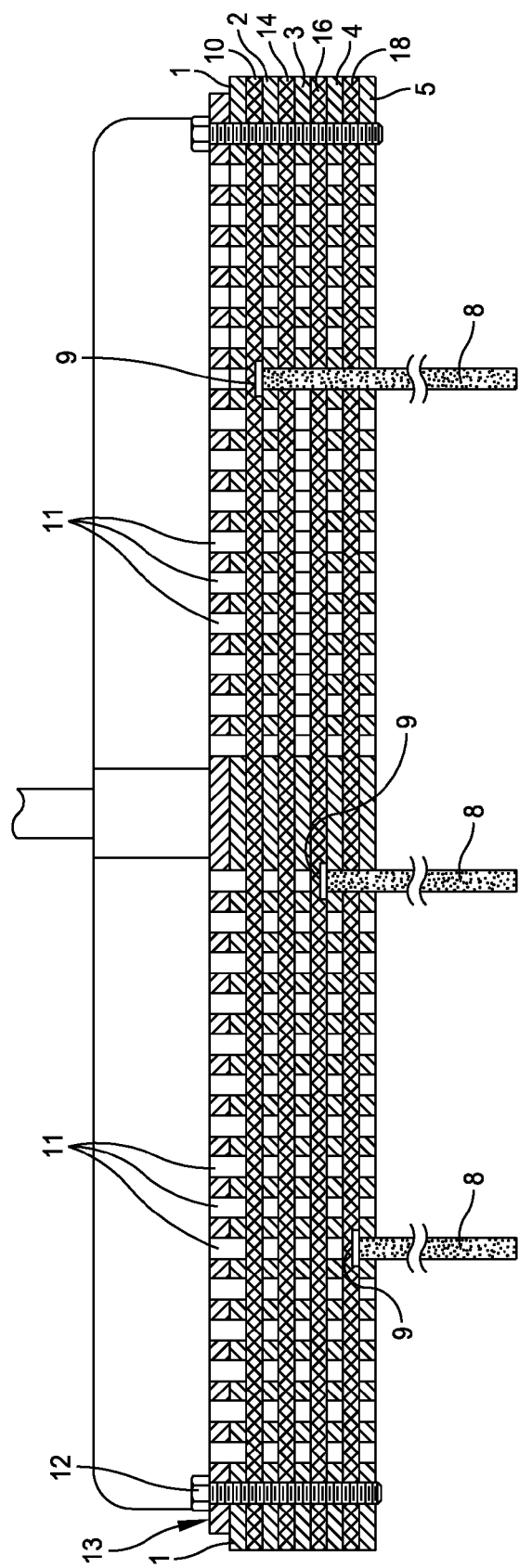
FIG. 4A is a cross-sectional view through the tube sheet of FIG. 4 as taken along line 4A-4A.

FIGS. 4 and 4A shows a fourth version of a multi-segmented tube sheet, where n=2 is the minimum number of sheets and there is no upper limit; and the minimum tube count n=1 and there is no upper limit. In this particular embodiment the multi-segmented tube sheet is shown with six sheets identified as sheets 1 through 5 arranged such that the tubes 8 (themselves at times filtration elements, other times not) are installed. In addition there are shown multiple media sheets 10, 14, 16 and 18 disposed between adjacent sheets. In this embodiment a flanged surface may be provided at any of the main sheets 1 through 5 preferably below sheet 1. Refer to FIG. 4A for examples showing different locations of the tube flange 9. Again, the first sheet 1 in this case may act as a hold down to the tubular elements 8 and all other sheets including the additional layer of media sheets. These media sheets may act as a filtration barrier or a conversion medium to the process media as it passes from the unprocessed side to the processed side, and which may or may not be installed at this location depending on the desired action on the media as it transitions from the primary to the secondary side of the tube sheet. The multiple media sheets may provide progressively finer filter media along the tube sheet between primary and secondary sides. The tube sheet stack in the assembled form may be permanently constructed as with rivets, weld, solder, braze, epoxy, etc. (see fasteners 12) or constructed with removable fasteners such as bolts, screws, removable rivets, etc. or simply floated between some reference points to facilitate loading of the media while simultaneously serving the purpose of a traditional tube sheet acting simply as a bulkhead and the demarcation location between the primary and secondary sides of the tube sheet.

Referring now to FIG. 5, a typical tube sheet filter apparatus is shown of the general type to which the present invention is directed to improve upon by the incorporation of the improved tube sheet of the present invention. The filter apparatus is designated generally by the reference numeral 20 and includes a filter tank 22, which is typically of generally vertical cylindrical configuration. Filter tank 22 is configured with an upper section 24 that may have a closed off upper head portion and an open ended lower portion, and a lower section 28 that may have an open ended upper portion in facing alignment with the upper section of the tank and an oval shaped lower portion. The respective upper and lower sections 24 and 28 may be respectively provided with annular flanges (not shown) extending outwardly adjacent the open ends thereof. Such flanges are typically provided with aligned openings formed therein for receipt of fastening means 12 (see FIG. 4).

FIG. 5 also illustrates a substantially horizontal plate or tube sheet indicated generally at 32 and positioned within the filter tank 22 such that the outer edges thereof are received and retained in place between flanges through a generally horizontal plane therebetween. Tube sheet 32 which is formed with openings 34 (analogous to holes 11) extending therethrough, divides the filter tank 22 into an upper effluent compartment 36 and a lower influent compartment 38. The tube sheet 32 shown in FIG. 5 may be considered to be the same as any one of the tube sheets previously described in FIGS. 1-4 herein.

In FIG. 5 a plurality of filter elements or filter tubes 8 are supported from the tube sheet 32 and extend downwardly into the influent compartment 38. These filter elements are typically of the stainless mesh or wire wound type, an example of which is disclosed in U.S. Pat. No. 3,779,386. The lower ends of the filter elements 8 are preferably blocked off by some suitable means. In the embodiments illustrated herein only a limited number of tubes are shown, but in a typical installation up to hundreds of tubes are supported from a tube sheet or between spaced apart respective tube sheets. Also, the tube sheet may be supported horizontally, vertically or in another orientation.

An effluent conduit 48 extends outwardly from the upper section 24 of filter tank 22 in fluid communication with the interior of effluent compartment 36 for withdrawing the treated liquid therefrom. An influent conduit 50 extends outwardly from the lower portion of section 28 in fluid communication with influent compartment 38. A drain fitting (not shown) may extend from the lowermost end of lower section 28 through which the filter tank 12 may be drained. In another embodiment of the present invention the effluent and influent ports may be at the same side of the tank structure such as in a structure like that shown in U.S. Pat. No. 5,128,038.

The brief description of the operation of filter apparatus 20 which hereinbelow follows is for the purpose of setting forth the general nature of such operation and is not intended to be a detailed disclosure of such operation. In operation, the outer surfaces of the filter elements 8 are typically precoated with a precoat layer of particles, such as finely divided ion exchange resin particles, by passing a slurry of such particles into and through influent compartment 38 such that the particles attach to and form a precoat layer on the outer surface of the filter elements. During the service cycle, untreated liquid is directed through influent conduit 50 into influent compartment 38. The pressure of the incoming untreated liquid forces it through the precoat layer, the filter elements 8, and the effluent compartment 36 into the effluent conduit 48. As the untreated liquid passes through the precoat layer, an ion exchange reaction takes place to remove dissolved impurities from the liquid. In addition, undissolved impurities are removed from the untreated liquid by virtue of the liquid passing through the precoat layer of finely divided resin particles and filter elements 8. A filter cake, consisting of undissolved impurities, builds up within and on the precoat layer as the service cycle continues. As is well known in the art, the precoat layer may contain various combinations of reactive materials, such as ion exchange resins, activated carbon etc., and non-reactive materials.

Eventually, the precoat layer will become exhausted and must be thoroughly removed and discarded. At such time, the service cycle is stopped and it is necessary to clean the filter elements 8, by removing the filter cake and the precoat layer therefrom during a backwash cycle, before the filter elements 8 are once again precoated and returned to service. During the backwash cycle, the liquid in the filter tank 22 is drained down and the void space thereabove is pressurized through the addition of pressurized gas into filter tank 12. The drain conduit is then opened and the backwash liquid in the filter tank is rapidly drained with the assistance of the pressurized gas therein to dislodge and remove the filter cake and precoat layer from the filter tank.

Referring now to FIG. 6, which is essentially a like embodiment to that shown in FIG. 3A where layer 10' is a media layer in the form of a nanotubular structure within a platinum amalgam, within which, an ion exchange takes place as the fluid passes through this layer, while passing through the tube sheet structure. The advantage of processing this step of an ion exchange within the tube sheet structure is that there is a defined segmentation of the fluid flow by the tube sheet structure, where n=1 minimum openings with no upper limit, and therefore, 1/n fluid flow will be treated by 1/n surface area exposed to this flow due to the interstitial placement of the nanotubular structure. This layer serves as the site of catalysis in a redox reaction providing both expanded surface area and the requisite catalyst, in this case platinum, to enable a reaction that occurs faster and with less energy. Since in the reaction, catalysts regenerate, only a small amount is generally required.

One further embodiment is where all layers are considered as metallic layers. For example, and with reference to the embodiment shown in FIGS. 2 and 2A, the layers 1-6 can be formed of copper sheets with an interstitial layer 10 between those sheets of a woven screen or sintered particles, also of copper, that performs some filtration or acts as an orifice or a shock absorbing barrier. In this embodiment, all of the sheets may be a copper alloy.

Figure 7:
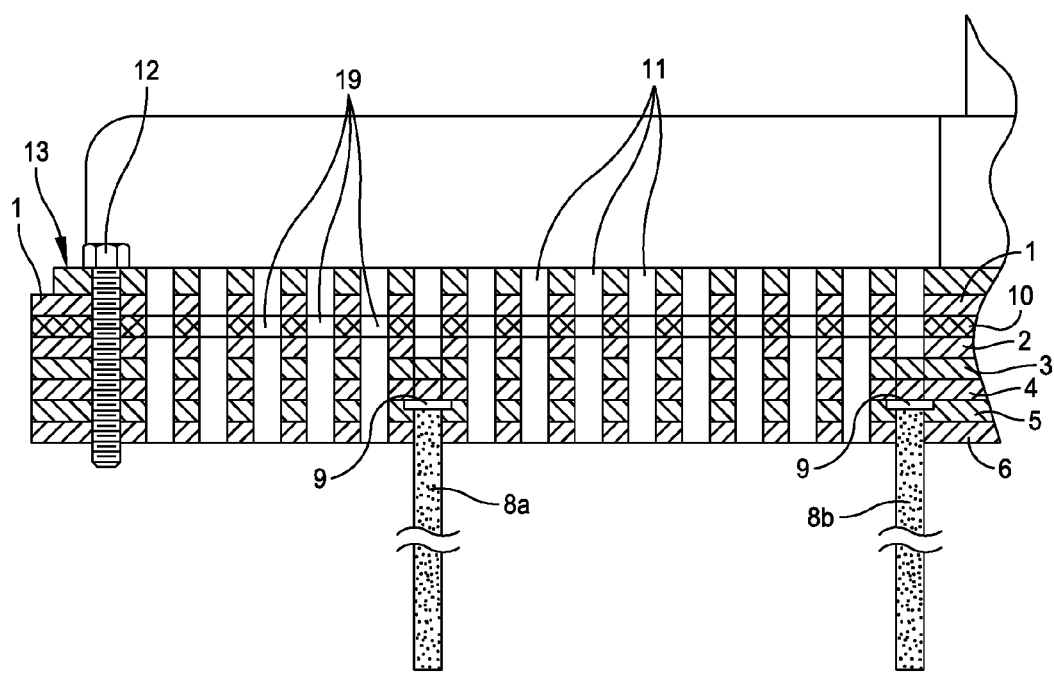
FIG. 7 is a cross-sectional view through an alternate embodiment of a tube sheet.

A further embodiment that is contemplated provides the media layer as one that can control the flow level through the tube sheet by means of specific restrictions imposed by this layer. Refer to FIG. 7 herein. For example, the media layer 10 may be solid in configuration but provided with one or more restricting orifices 19 through the surface thereof to control flow rate. The size (diameter) of each orifice 19, as well as the number of orifices determines the flow rate through the tube sheet. Such a media layer thus functions as a throttling mechanism within the tube sheet itself so as to modulate the output flow given some input condition such as flow and/or pressure. A media layer with one or more orifices 19 can also function for filtration through the non-orifice locations. Thus, any one media layer may be considered as having multiple functions. In FIG. 7 the orifices 19 are shown as aligned with the holes 11, however, in other embodiments the orifices may not be so aligned. If the layer 10 is somewhat porous then orifices can be provided at many different locations in layer 10.

Another embodiment for the media layer relates to the ability to provide a magnetic characteristic. In other words the concept is to construct layer 10, such as in FIGS. 2 and 2A (or in other embodiments shown herein) from a permanent magnet or forming it from a material that could be imbued with magnetic properties. A magnetic circuit could be coupled to the layer 10 to provide a magnetism effect to the layer. This creates the ability to filter out magnetic particulates as they flow through the tube sheet whether using an external excitation or using a permanent magnet arrangement. For external excitation reference may be made to co-pending application Ser. No. 14/535,655 in the embodiment shown in FIG. 6 therein where an external stimulus device is used to impart a characteristic to the media layer such as a magnetic property. Thus, in one embodiment, the media layer 10 can be constructed of a permanent magnetic material.

In this case, in the embodiment of FIGS. 2 and 2A, the layers 1 and 2 can be constructed of a non-magnetic material so as not to magnify the strength of the magnetic layer 10. Alternatively, the layers 1 and/or 2 may be constructed of a material that exhibits magnetic susceptibility, such as those with ferromagnetic (e.g. iron), ferrimagnetic (e.g. magnetite), or antiferromagnetic (e.g. iron manganese, nickel oxide) qualities and, in the case of antiferromagnetic, organic molecules (e.g. 5-dehydro-m-xylene).

Still another embodiment contemplates providing a passive layer as a dosing layer. Referring, for example, to FIGS. 2 and 2A, the layer 10 may be an interstitial sheet that has been impregnated with a medicine or a chemical that releases over time or when the temperature becomes elevated. This concept may be embodied in a device such as in a transfusion machine or where a patient with hypothermia is being treated and one prefers a compact device that can readily release medication as soon as, for example, the patient's blood temperature raises enough. This is thus in the form of a portable multi-purpose rescue device to warm blood as in a triage on the side of a mountain when rescuing avalanche victims. Moreover, in concert with the application of a medicine or chemical, the medial layer can also be constructed using the aforementioned orifice plate to modulate flow. There is thus provided a treated layer now placed within the tube sheet itself and that provides a device that will modulate the output (medicine or chemical) given some input condition such as flow and temperature. Again, this is an example of a multiple function of the media layer.

In still another embodiment for practicing the present invention there is provided an active layer that functions as a UV light delivery zone. In this regard refer to a further version of a tube sheet as illustrated in FIG. 7 herein. In this version layer 4, or other layers, may be a natural or synthetic quartz or engineered glass product that selectively transmits in the UV spectrum. The UV dose is delivered to this interstitial location via some number, where n=1 with no upper limit of fiber-optic tubes 8 into the zone between layers 3 and 5, in other words into layer 4. As flow passes through the tube sheet, it passes through the intersticies of layers 3 to 5. The flow passing will be dosed with UV light emanating from layer 4, and any living matter will have its DNA disrupted or possibly annihilated in an example of this embodiment that may be part of a sanitation device. In FIG. 7 there is provided fiber optic elements or tubes 8a, 8b. The layer 3 reflects into layer 4 but only at the tubes 8a, 8b. At the location of the tubes aligned holes in other layers are optional.

Figure 8:
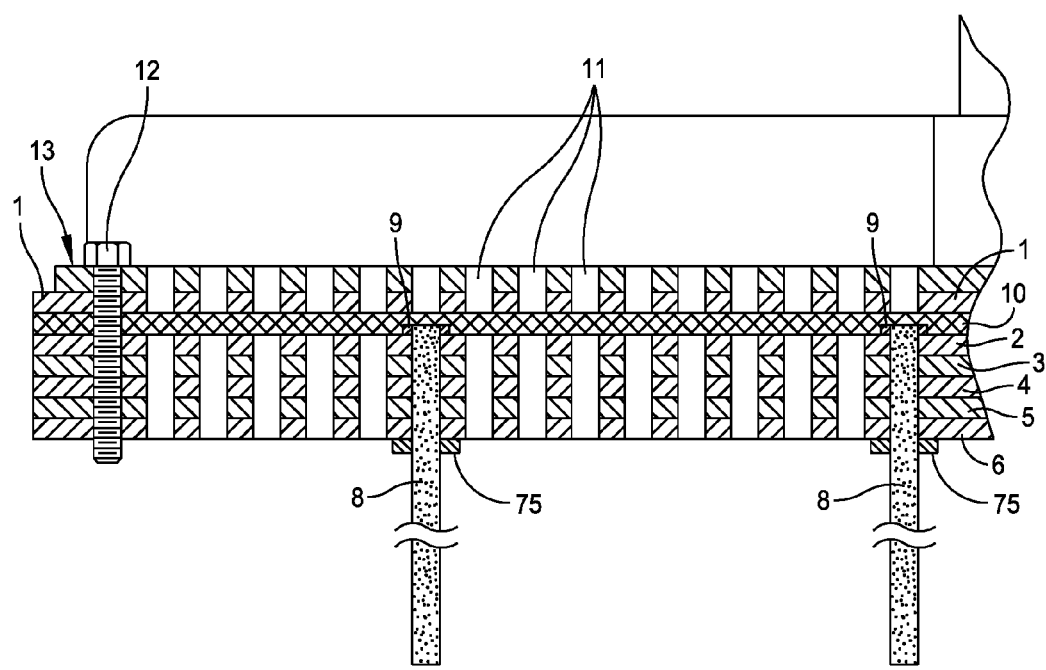
FIG. 8 is a fragmentary cross-sectional view showing another embodiment of the present invention including a securing piece associated with the filter tube.
Figure 9:
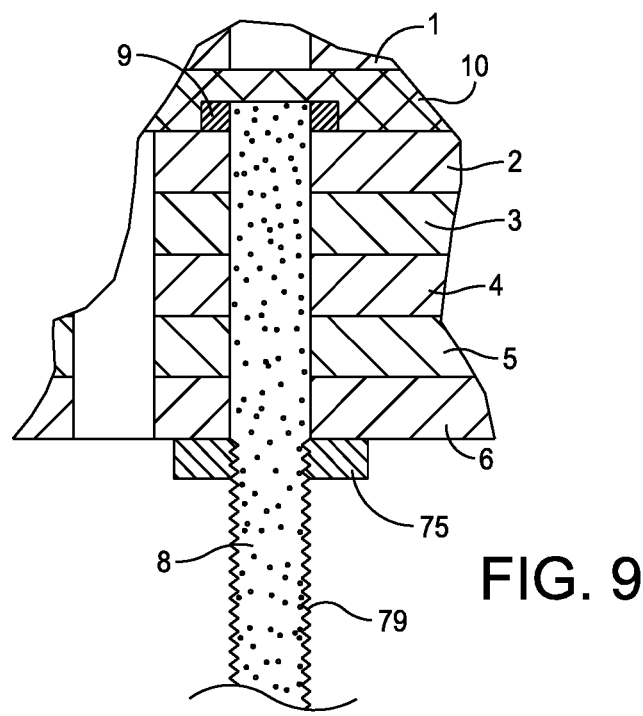
FIG. 9 is an enlarged cross-sectional view showing the construction at one filter tube and employing a securing nut.
Figure 10:
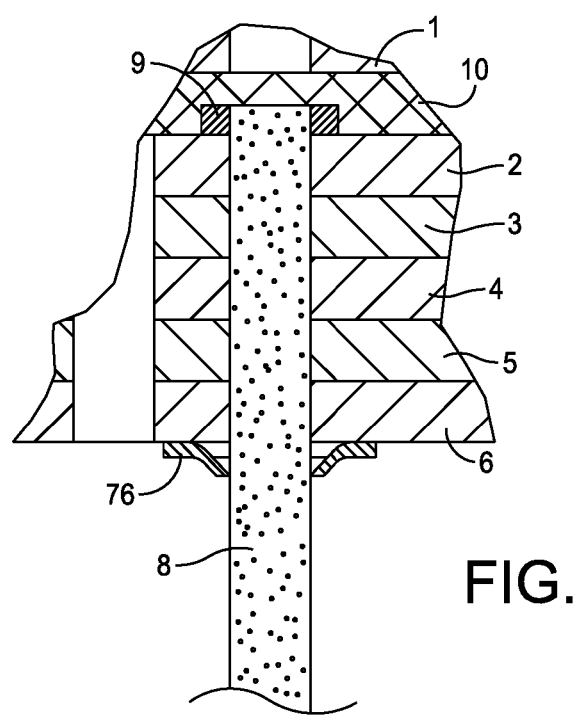
FIG. 10 an enlarged cross-sectional view showing the construction at one filter tube and employing a push nut.
Figure 10A:
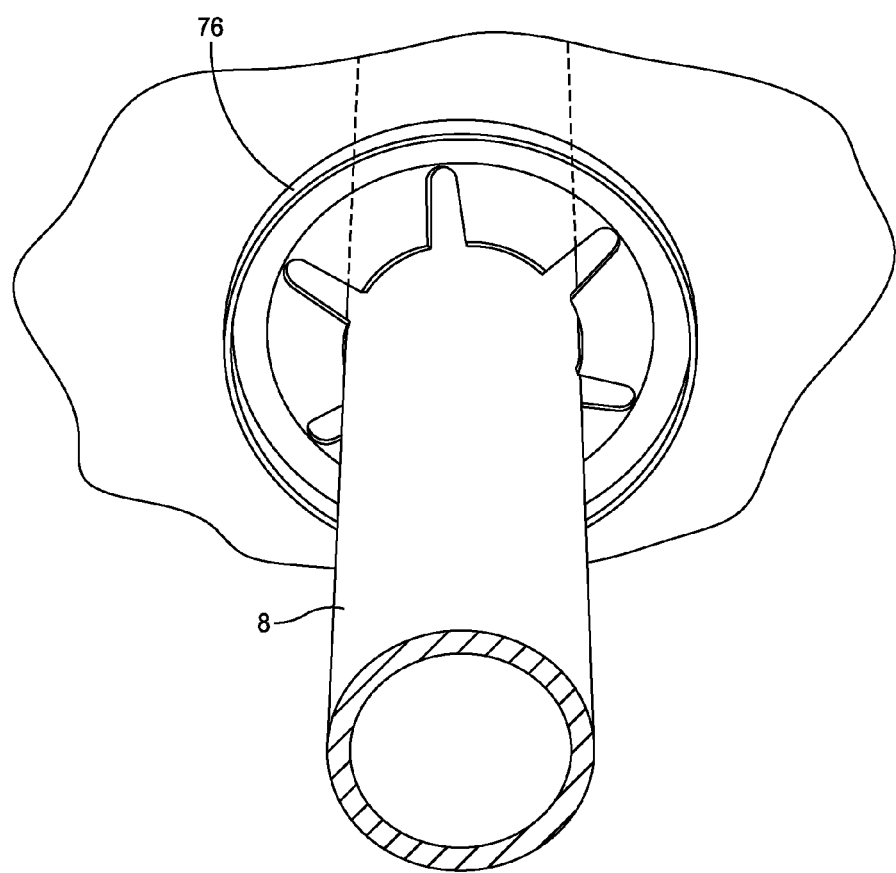
FIG. 10A is a fragmentary perspective view illustrating the push nut disposed on a filter tube.
Figure 11:
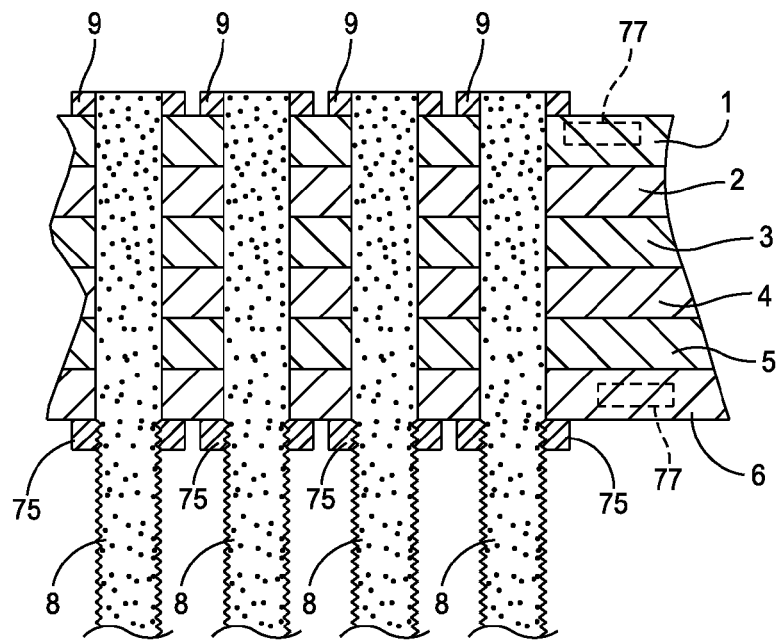
FIG. 11 is a fragmentary cross-sectional view of another embodiment of the present invention employing the securing piece.
Figure 12:
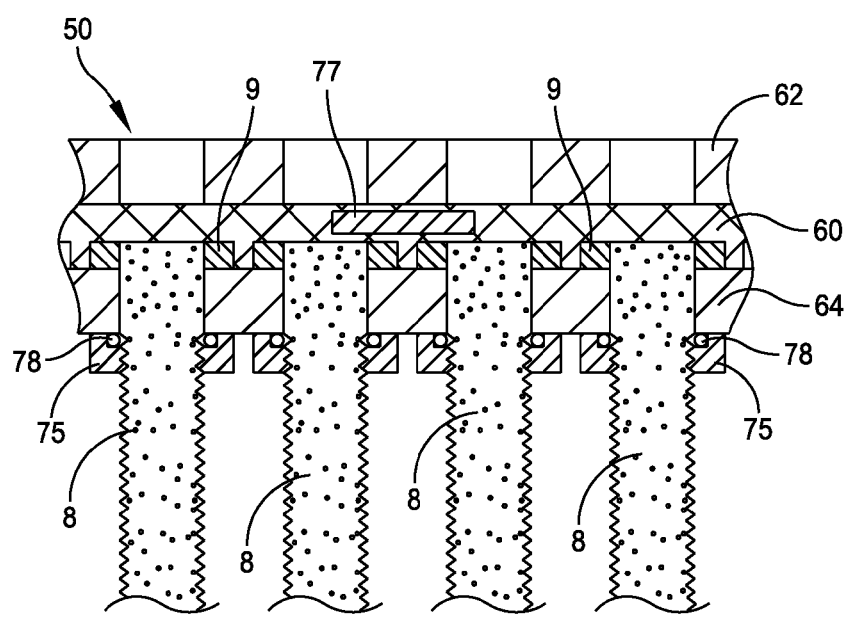
FIG. 12 is a fragmentary cross-sectional view showing the use of the securing piece associated with each filter tube and a sensor.

An alternate embodiment of the present invention is now illustrated in FIGS. 8-12. FIG. 8 is a fragmentary cross-sectional view showing another embodiment of the present invention including a securing piece associated with the filter tube. FIG. 9 is an enlarged cross-sectional view showing the construction at one filter tube and employing a securing nut. FIG. 10 an enlarged cross-sectional view showing the construction at one filter tube and employing a push nut. FIG. 10A is a fragmentary perspective view illustrating the push nut disposed on a filter tube. FIG. 11 is a fragmentary cross-sectional view of another embodiment of the present invention employing the securing piece. FIG. 12 is a fragmentary cross-sectional view showing the use of the securing piece associated with each filter tube and a sensor. The embodiments described in FIGS. 8-12 represent a further improvement to the tube sheet construction. This primarily involves use of a securing piece that is constructed and arranged to be disposed about the tubular element or filter tube and functions, in concert with, the flanged end of the elongated tubular element to provide a compressive force against the tube sheet segments that are disposed between the flanged top end and the securing piece. This construction may be used in a tube sheet construction such as illustrated in the fragmentary cross-sectional view of FIG.

8. In this particular embodiment the tube sheet construction is shown as including a media layer 10, although, the principles of the present invention may also be used in a tube sheet construction where there is no media layer provided.

The fragmentary cross-sectional view of FIG. 8 illustrates the flanged end at 9. This may be constructed of a grommet that is crimped about an end of the elongated hollow tubular element 8. In other embodiments of the present invention, this flanged member 9 may also be crimped about other locations along the elongated tubular element 8. FIG. 8 also illustrates a securing piece in the form of a nut 75 that is threadedly engaged with the element 8. In this regard, refer to the somewhat more detailed fragmentary cross-sectional view of FIG. 9 illustrating the nut at 75 engaged with the elongated tubular shaft 8 which has external threads 79. Reference may also now be made to the fragmentary cross-sectional view of FIG. 10 to show a different embodiment of the securing piece. This is illustrated as in the form of a push nut 76. Refer also to the fragmentary perspective view of FIG. 10A that shows further details of the push nut 76. The push nut 76 functions so that it can be forced onto the shaft of the filter tube but is constructed so that it is locked in place once pushed on and not easily disengaged from the filter tube 8. In FIG. 10 the filter tube 8 is shown as having a smooth outer surface. However in another embodiment of the present invention, it may be provided with small circular indentation rings that assist in the positioning and engagement of the push nut 76 with the filter tube 8.

Reference is now made to FIG. 11 which is a further fragmentary cross-sectional view showing multiple tubular elements 8 with a grommet or flanged end illustrated at 9 and with a securing piece in the form of a nut 75 under the layer 6. The flanged end 9 is disposed above the top layer 1 of the multiple tube sheet segments. The nut 75 is disposed under the bottommost layer 6 of the plurality separate planar tube sheet segments. By tightening the nut 75, there is a compressive force between the nut 75 and the flange 9 providing a compression of the tube sheet segments therebetween. Even though a cover is provided with additional fasteners 12, the tube sheet segments may be relatively large in diameter and by providing the securing pieces as described herein, there is additional compression and additional tension on the tube sheet segments at virtually every location of the filter tubes. Although a securing piece is illustrated at each of the tubes 8 in FIG. 11, it is also possible to provide a securing piece at only predetermined ones of the elongated filter tubes 8. The use of securing pieces can be arranged to provide a series of securing pieces spread throughout the tube sheet construction, each associated with a filter tube as illustrated, so that there are several locations where additional compression is applied. Also, the flanged end 9 is provided so that it engages firmly with a top surface of the engaged tube sheet segment by virtue of the hole in the segment being smaller than the diameter of the flanged end, leaving an annular engagement surface of the flanged end directly against the tube sheet segment surface; usually the upper surface thereof.

One particular advantage of the embodiment illustrated in FIG. 10 with the push nut is that it makes the entire structure more tamper proof or tamper resistant. As also previously indicated, this combination of the flanged end and the securing piece introduces another level of tension for the securing of the tubes to the sheet segments.

Reference is now made to the fragmentary cross-sectional view of FIG. 12 which shows the principles of the flanged end and securing piece applied to a simplified tube sheet construction including layers 60, 62 and 64. In this embodiment there is also provided on each of the filter tubes 8, a flanged end at 9 and a securing piece at 75. In this particular embodiment there may also be provided an O-ring 78 between each of the securing nuts 75 and the layer 74. This O-ring 78 can provide additional sealing between each filter tube and the tube sheet construction. In addition, FIG. 12 also illustrates a sensor 77. Multiples sensors may be provided in the layer 60 although only one sensor 77 is shown in FIG. 12. This may be a temperature or pressure sensor or virtually any other type of sensor such as for flow control. In addition, as illustrated in dotted outline in FIG. 11, sensors 77 may also be provided in different layers of the tube sheet construction. In FIG. 12, the sensor 77 is illustrated in a media layer 60. In FIG. 11 the two sensors 77 shown in dotted outline are in respective planar tube sheet segments 1 and 6. by placing sensors at different locations within the tube sheet construction different parameters can be sensed such as different pressures or temperatures across the tube sheet construction.

Having now described a limited number of embodiments of the present invention, it should now be apparent to those skilled in the art that numerous other embodiments and modifications thereof are contemplated as falling within the scope of the present invention, as defined by the appended claims.

What is claimed is:

1. A tube sheet construction that is comprised of a plurality of separate planar tube sheet segments, multiple holes being provided in each planar tube sheet segment in a predetermined pattern, each hole for accommodating an elongated tubular element, an active planar layer disposed parallel with the plurality of separate tube sheet segments, and fasteners for securing all of the planar tube sheet segments and the active planar layer together and arranged so that all planar tube sheet segments and said active planar layer are maintained in intimate contact so as to form a solid tube sheet structure, said active layer comprising a UV light emanating layer that doses any fluid flow through the tube sheet construction with UV light emanating from the UV light emanating layer so as to disrupt or annihilate any living matter.

2. The tube sheet construction of claim 1 wherein all of the tube sheet segments are aligning so that the hole pattern of each segment aligns with the hole pattern in all other segments.

3. The tube sheet construction of claim 1 wherein each planar tube sheet segment is constructed of a metal material.

4. The tube sheet construction of claim 3 wherein the UV light emanating layer is disposed between adjacent planar tube sheet segments.

5. The tube sheet construction of claim 1 including a cover disposed over the planar tube sheet segment and at least one sensor element supported at one of the planar tube sheet segments.

6. The tube sheet construction of claim 1 including multiple sensor elements supported at respective planar tube sheet segments in order to sense parameters across the tube sheet construction.

7. The tube sheet construction of claim 1 wherein each said elongated tubular element has a flanged top end and a contiguous tubular shaft, and further including a securing piece constructed and arranged about the tubular shaft of the elongated tubular element and spaced below the flanged top end of the elongated tubular element, said securing piece for engagement with the tubular shaft to provide a compressive force against the tube sheet segments that are disposed between the flanged top end of the elongated tubular element and the securing piece wherein the securing piece comprises at least one of a threaded nut and a push nut.

8. The tube sheet construction of claim 1 wherein the UV light emanating layer is comprised of one of a natural quartz and a synthetic quartz that transmits in the UV spectrum.

9. The tube sheet construction of claim 1 wherein the UV light emanating layer is comprised of one of an engineered glass product that transmits in the UV spectrum.

10. The tube sheet construction of claim 1 wherein each said elongated tubular element has a contiguous tubular shaft with a top end, and the top end is disposed supported at a predetermined planar tube sheet segment below the UV light emanating layer.

11. The tube sheet construction of claim 10 wherein the UV light emanating layer is disposed between adjacent planar tube sheet segments including the predetermined planar tube sheet segment and an overlying planar tube sheet segment.

12. The tube sheet construction of claim 11 wherein the top end of the tubular shaft includes a flanged top end that is disposed between the predetermined planar tube sheet segment and the UV light emanating layer.

* * * * *